US008227531B2

(12) United States Patent
Lederer et al.

(10) Patent No.: US 8,227,531 B2
(45) Date of Patent: Jul. 24, 2012

(54) CROSSLINKED, ULTRAHIGH MOLECULAR WEIGHT POLYETHYLENE (UHMW-PE)

(76) Inventors: Klaus Lederer, Kalwang (AT); Christian Wolf, Graz (AT)

( * ) Notice: Subject to any disclaimer, the term of this patent is extended or adjusted under 35 U.S.C. 154(b) by 5 days.

(21) Appl. No.: 11/282,448

(22) Filed: Nov. 17, 2005

(65) Prior Publication Data

US 2006/0264541 A1     Nov. 23, 2006

Related U.S. Application Data

(63) Continuation of application No. PCT/AT2004/000133, filed on Apr. 22, 2004.

(30) Foreign Application Priority Data

May 19, 2003   (AT) ..................... 769/2003

(51) Int. Cl.
C08K 5/1545   (2006.01)
C08K 5/13     (2006.01)
C08L 23/04    (2006.01)
C08L 23/06    (2006.01)

(52) U.S. Cl. ........ 524/110; 524/107; 524/323; 524/324; 524/339; 524/334; 524/585; 522/161

(58) Field of Classification Search .................. 523/319, 523/340, 347, 344; 524/585, 110, 324; 522/161
See application file for complete search history.

(56) References Cited

U.S. PATENT DOCUMENTS

| | | | | |
|---|---|---|---|---|
| 5,827,904 A | * | 10/1998 | Hahn | 523/113 |
| 6,017,975 A | * | 1/2000 | Saum et al. | 522/161 |
| 6,228,900 B1 | * | 5/2001 | Shen et al. | 522/153 |
| 6,277,390 B1 | * | 8/2001 | Schaffner | 424/422 |
| 6,448,315 B1 | * | 9/2002 | Lidgren et al. | 524/110 |
| 6,547,828 B2 | * | 4/2003 | Scott et al. | 623/66.1 |
| 7,214,764 B2 | * | 5/2007 | King | 528/480 |
| 7,335,697 B2 | * | 2/2008 | King et al. | 524/585 |
| 7,431,874 B2 | * | 10/2008 | Muratoglu et al. | 264/235 |
| 2003/0212161 A1 | * | 11/2003 | McKellop et al. | 522/3 |

FOREIGN PATENT DOCUMENTS

| | | | |
|---|---|---|---|
| EP | 613 923 A1 | * | 2/1994 |
| EP | 0995449 A1 | | 4/2000 |
| JP | 2001-212837 A | * | 8/2001 |
| WO | 00/49079 A1 | | 8/2000 |
| WO | WO 00/49079 | * | 8/2000 |
| WO | WO-2004/064618 A2 | | 8/2004 |

OTHER PUBLICATIONS

Wolf et al. J. Mat. Sci: Materials in Medicine, 2002, 13, 185-189.*
Oral E. et al., Biomaterials, 2004, 25, 5515-5522.*
Costa, L., et al., Biomaterials, 2001, 22, 307-315.*
Blunn, G., et al. Journal of Bone and Joint Surgery, Sep. 2002, 84(7), 946-949.*
Parth, M., International J. of Polymer Anal. Charact., 2003, 8, 175-186.*
Parth, M. et al., J. of Materials Science: Materials in Medicine, 2002, 13, 917-921.*
Reno, F. et al., Biomaterials, 2004, 25, 995-1001.*
Shibata, N. et al., J. Biomedical Materials Research, Part A, 2003, 67A(1), 276-284.*
Tomita, N. et al., J. Biomedical Materials Research, 1999, 48(4), 474-478.*
Wolf, C. et al., "Tests of biocompatibility of alpha-tocopherol with respect to the use of a stabilizer in ultrahigh molecular weight polyethylene for articulating surfaces in joint endoprostheses", Journal of Materials Science: Materials in Medicine, vol. 13, pp. 701-705, 2002.
Wolf, C. et al., "Examination of the suitability of alpha-tocopherol as a stabilizer for ultra-high molecular weight polyethylene used for articulating surfaces in joint endoprostheses", Journal of Materials Science: Materials in Medicine, vol. 13, pp. 183-189, 2002.

* cited by examiner

*Primary Examiner* — Rip A. Lee
(74) *Attorney, Agent, or Firm* — Birch, Stewart, Kolasch & Birch, LLP

(57) ABSTRACT

Crosslinked ultra-high molecular weight polyethylene (UHMW-PE) is disclosed, as well as molded bodies made from the UHMW-PE and a process for making such UHMWE-PE.

8 Claims, 9 Drawing Sheets

CROSSLINKED, ULTRAHIGH MOLECULAR WEIGHT POLYETHYLENE (UHMW-PE)

This application is a Continuation of co-pending PCT International Application No. PCT/A04/00133 filed on Apr. 22, 2004, which designated the United States, and on which priority is claimed under 35 U.S.C. §120, the entire contents of which are hereby incorporated by reference.

The present invention relates to a new crosslinked ultra-high molecular weight polyethylene (UHMW-PE). Furthermore, the invention relates to moulded bodies made of this UHMW-PE as well as to processes by means of which said UHMW-PE is obtainable.

Approximately 70% of all hip and knee endoprostheses used worldwide are equipped with gliding surfaces made of UHMW-PE. Although these have been used successfully in clinical applications for more than 30 years now, their lifetime is usually limited to 10 to 15 years. The cause for this limited lifetime lies in mechanisms of oxidative damage to the UHMW-PE in the human body, which can lead to a dramating increase in PE-abrasion, followed by inflammations in the surroundings of the implant. In most cases, this necessitates expensive revision surgery.

Extensive studies (C. Wolf et al., J. Mat. Sci.: Mat. in Med. 13 (2002), 185-189; C. Wolf et al., J. Mat. Sci.: Mat. in Med. 13 (2002), 701-705) have shown that damage to UHMW-PE gliding surfaces as a result of oxidation is markedly delayed by adding the natural antioxidant $\alpha$-tocopherol (vitamin E), whereby an increase in the lifetime of such prostheses by a factor of 2.5 can be expected.

In EP 0 995 449 A, such a UHMW polyethylene is described, which is doped by the deposition of vitamin E dissolved or suspended in a liquid on the powdery base material.

According to WO 00/49079 A, a UHMW-PE doped with an antioxidant such as $\alpha$-tocopherol is produced by mixing the polyethylene particles with the antioxidant and $CO_2$ under supercritical fluid conditions at elevated temperature and pressure in order to form a supercritical mixture which subsequently is expanded, whereby the $CO_2$ evaporates.

In both above-described processes, the doped UHMW-PE is subsequently shaped by extrusion, pressing and the like into bars and blocks for further processing.

In recent years, irradiated UHMW-PE has gained more and more importance as a further material for gliding surfaces of endoprostheses. By treatment with high-energy radiation, the abrasion behaviour of UHMW-PE can be significantly improved. The irradiation process is followed by a specific annealing step resulting in further crosslinking as well as in a saturation of the free radicals formed by the radiation. Since the free radicals are considered to be the starting point of oxidation, this leads to an increased oxidation resistance of the material. If, however, the chemical structure of the crosslinked UHMW-PE is examined, it is apparent that said crosslinked UHMW-PE is virtually identical in chemical terms to the previously used standard UHMW-PE (however, the crosslinked UHMW-PE exhibits tertiary C-atoms as cross-link points which are even more susceptible to oxidative attack than the secondary C-atoms of the main chain). Accordingly, an addition of $\alpha$-tocopherol should substantially enhance the oxidation resistance of crosslinked UHMW-PE.

With irradiated PE, it is not possible to add $\alpha$-tocopherol to the PE-powder prior to the actual processing, as opposed to conventional UHMW-PE, since said $\alpha$-tocopherol inhibits crosslinking during the irradiation process and also during the annealing process, whereby it itself is degraded to a large extent.

It is the object of the invention to provide a crosslinked ultra-high molecular weight polyethylene whose oxidation resistance is enhanced, i.e. which has been stabilized. Thereby, in particular a longer lifetime of moulded bodies made of said UHMW-PE, especially of those designed as endoprostheses, is to be achieved. Furthermore, it is the object of the invention to provide a process by means of which the UHMW-PE according to the invention is obtainable.

According to the invention, the first object is achieved by means of a crosslinked ultra-high molecular weight polyethylene containing $\alpha$-tocopherol as a stabilizer.

The process according to the invention by means of which the UHMW-PE containing $\alpha$-tocopherol is obtainable is characterized in that the $\alpha$-tocopherol is allowed to diffuse into the crosslinked ultra-high molecular weight polyethylene.

Due to the prevention of the crosslinking of polyethylene and the degradation of $\alpha$-tocopherol, the introduction thereof into the UHMW-PE can occur only after the manufacturing steps performed on the irradiated semifinished product or on the finished final product. It has been shown that the physical transport phenomenon of diffusion can be employed in a goal-oriented manner in order to introduce $\alpha$-tocopherol into the crosslinked UHMW-PE. Thereby, the concentration of $\alpha$-tocopherol can be influenced by varying the process parameters (temperature, diffusion time).

In a preferred embodiment of the process, the inward diffusion is carried out under an inert gas atmosphere.

The inward diffusion of $\alpha$-tocopherol is preferably carried out at a temperature ranging from 100 to 200° C.

Preferably, the polyethylene is annealed under an inert gas atmosphere following the inward diffusion of $\alpha$-tocopherol. This leads to a uniform distribution of $\alpha$-tocopherol in the polyethylene, which at first is introduced by sorption and diffusion essentially only in the edge and surface areas of the crosslinked UHMW-PE.

Annealing of the polyethylene is preferably carried out at a temperature ranging from 160 to 200° C.

According to a preferred embodiment of the invention, the $\alpha$-tocopherol is allowed to diffuse into the polyethylene at 130° C. for 60 minutes, which polyethylene is subsequently annealed at 200° C. for 24 hours.

Furthermore, the crosslinked ultra-high molecular weight polyethylene according to the invention is obtainable by allowing the $\alpha$-tocopherol to diffuse into the polyethylene in the presence of supercritical $CO_2$.

$CO_2$ can be transformed into the supercritical state with relative ease and quickly diffuses into polymers due to its small molecular dimensions. In addition, it is nontoxic, non-inflammable, environmentally friendly and inexpensive. Vitamin E is soluble in supercritical $CO_2$ according to the following correlation (W. Chrastil, J. Phys. Chem. 86(15), 1982, 3016-3021):

$$C = d^{8.231} \cdot e^{(-17353.5/T + 0.646)}$$

wherein c represents the concentration [g/l of $\alpha$-tocopherol in $CO_2$, d [g/l] represents the density of $CO_2$ and T represents the temperature in K.

Preferably, the diffusion of $\alpha$-tocopherol into the polyethylene is carried out at a temperature ranging from 100 to 180° C.

The diffusion of $\alpha$-tocopherol into the polyethylene is preferably carried out at a pressure ranging from 150 to 300 bar.

Preferably, the temperature adjusted during the diffusion of α-tocopherol into the polyethylene is maintained during the expansion process in order to avoid structural changes in the UHMW-PE.

According to another aspect, the invention relates to moulded bodies made of the UHMW-PE according to the invention, in particular to those designed as an endoprosthesis.

Below, the invention is illustrated in further detail by way of the examples and FIGS. 1-9.

MATERIAL AND GENERAL MEASURING METHODOLOGY

The irradiated UHMW-PE used in the assays was Durasul from Messrs. Centerpulse, Winterthur, Switzerland. Cubes with an edge length of 20 mm were chosen as shapes for the test specimens.

In order to determine the distribution of α-tocopherol, the cubes were cut in the middle after the experiments and a film having a thickness of approx. 200 μm was planed from a cut surface, using a microtome cutter. With the aid of an FTIR-microscope, said film was then subjected from one edge to the other to a central Linescan with a distance between measuring points of 300 μm. The α-tocopherol concentration at the respective measuring points was determined by the ratio of the peak at 1230-1279 $cm^{-1}$, which peak was caused by the α-tocopherol, to the PE-peak at 2020 $cm^{-1}$. This concentration was plotted in a chart over the distance from the lateral edges of the film, thus illustrating the concentration profile. The unit of concentration data is mass of α-tocopherol to mass of UHMW-PE in percent. In addition, the cubes were weighed prior to and after the experiments and the total concentration of α-tocopherol was determined.

Introduction of α-Tocopherol into Crosslinked UHMW-PE by Diffusion

The attempt was made to introduce α-tocopherol into the Durasul cubes by simple inward diffusion. For this purpose, the cubes were placed into an autoclave which was filled with pure α-tocopherol. Subsequently, the autoclave was flushed with nitrogen for 10 minutes in order to generate an inert gas atmosphere. Upon completion of the flushing stage, the autoclave was closed and, via the supply of nitrogen, a pressure of approx. 15 bar was adjusted. A variation of the pressure in the autoclave vessel had no noticeable influence on the diffusion rate. The critical influencing factors temperature and duration of diffusion were varied in several experiments.

Results:

In the first part of this test series, the maximum temperature was set to be 100° C. The reason for this is that crosslinked UHMW-PE has sufficient dimensional stability up to this temperature, i.e., α-tocopherol can hence be added to a finished final product without the need for any further aftertreatment steps. Therefore, only the test period, i.e., the duration of diffusion, was modified.

Figure 1:
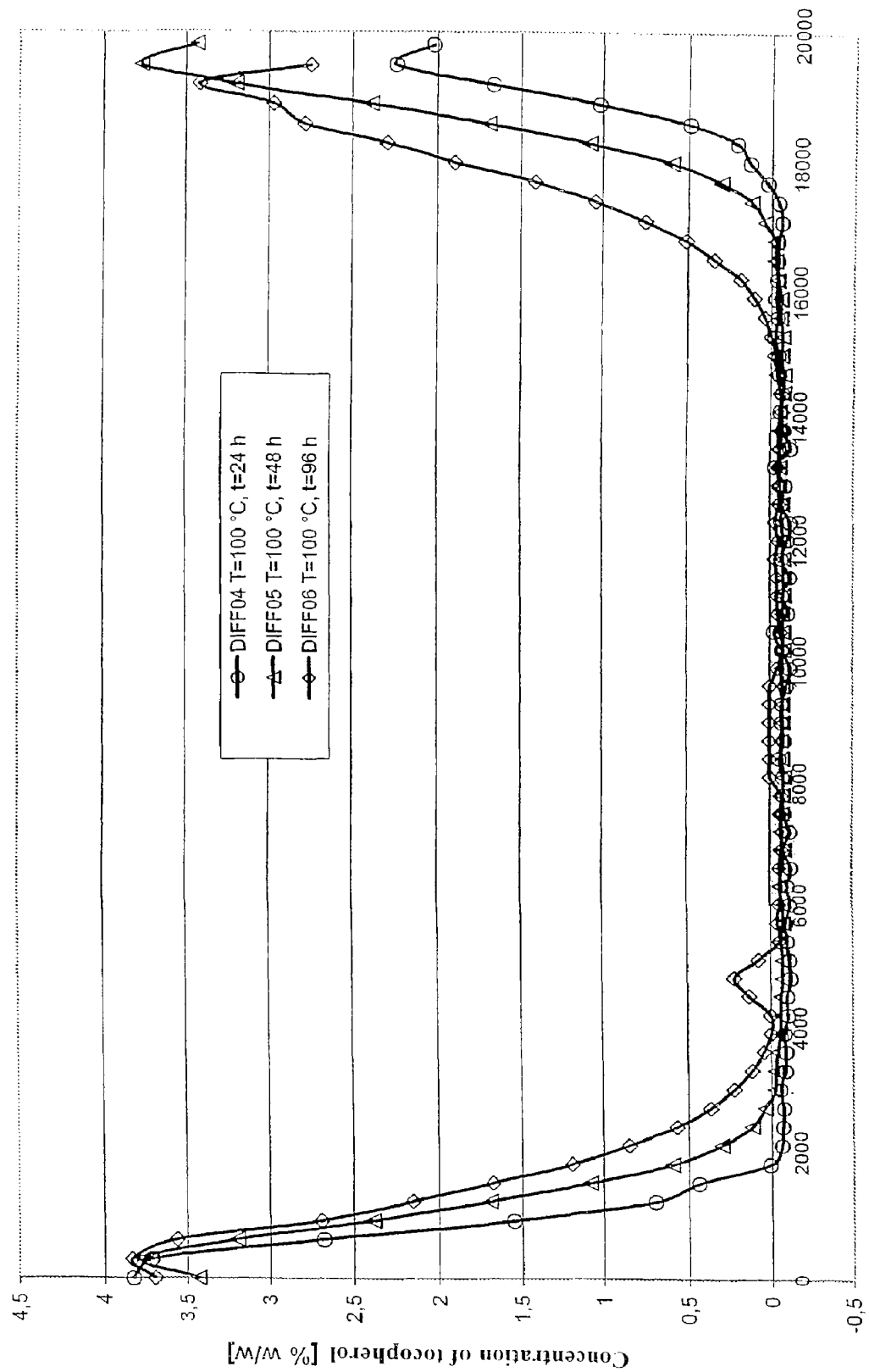
FIGS. 1-4 and 6-9 each illustrate a chart in which the concentration of α-tocopherol is plotted over the cross-section of a moulded body according to the invention.

The selected test parameters can be seen in Table 1, the concentration profiles associated therewith are illustrated in FIG. 1.

TABLE 1

| Experiment | Temperature [° C.] | Duration [h] | Total amount of α-tocopherol [% w/w] |
|---|---|---|---|
| DIFF04 | 100 | 24 | 1.27 |
| DIFF05 | 100 | 48 | 1.62 |
| DIFF06 | 100 | 96 | 1.82 |

Excessively large penetration depths were indeed not realized within a reasonable timeframe (see FIG. 1), however, the edge layer primarily affected by the oxidation was provided with a variable stabilizer concentration, thus creating a protection against oxidative degradation. Therefore, this method is suitable especially for finished products.

In a second test series, the experiments were carried out at elevated temperature. A clear increase in the diffusion rate as well as in the absorbed mass of α-tocopherol could be observed in particular when the crystallite melting range was reached.

Crystalline regions in the PE constitute diffusion barriers for the α-tocopherol; the migration of molecules occurs virtually exclusively in the amorphous phase. Melting of the crystalline regions thus leads to the observed strong increase in the diffusion rate—in addition to the accelerating effect of the elevated temperature.

The temperature increase furthermore results in a strong increase in the solubility of α-tocopherol in the UHMW-PE. At 200° C., up to 40% w/w of α-tocopherol could be incorporated in the polyethylene. However, these values are far beyond the saturation concentration at room temperature, consequently, the material was greatly "overloaded" with α-tocopherol at room temperature. After cooling, this caused an increased outward diffusion of vitamin E, the cubes "transpired" very strongly.

FIG. 1 and the above-described experiments show that the temperature significantly influences the edge and saturation concentrations, respectively, as well as the penetration depth, whereas, via the diffusion time, primarily the penetration depth can be adjusted.

It is true that a temperature increase significantly accelerates the diffusion process, as described above, however, also the edge concentration rises far beyond the range of a reasonable stabilizer concentration of approx. 0.2 to 1% at most. Without dilution of the α-tocopherol and thus the introduction. of a further component, it is impossible to accomplish a homogeneous vitamin E distribution within a reasonable timeframe and concentration range via simple diffusion. However, with respect to the use as an implant material, any introduction of a new component is to be avoided, since this might significantly aggravate the required approval procedure.

Figure 2:
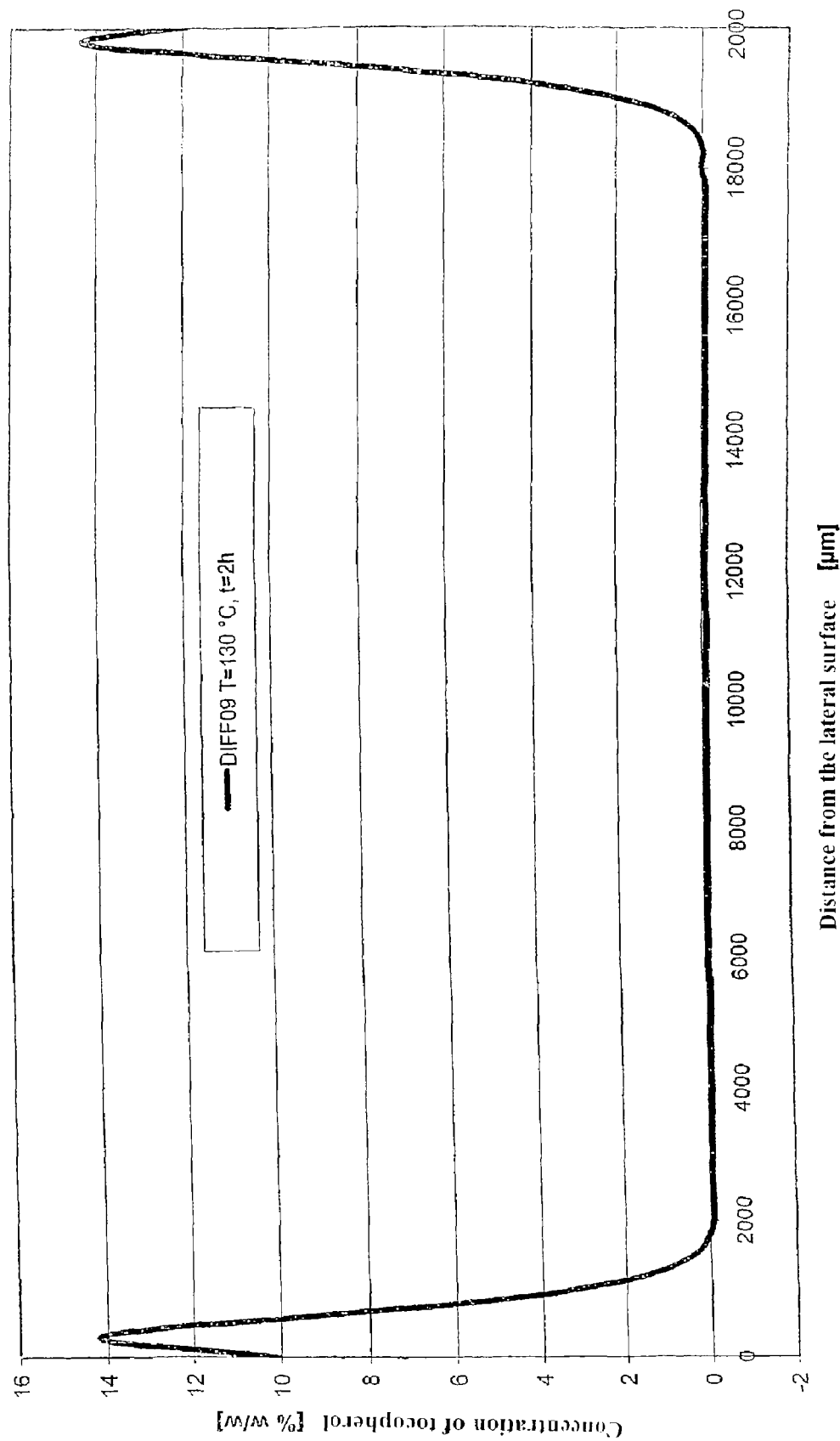
Figure 3:
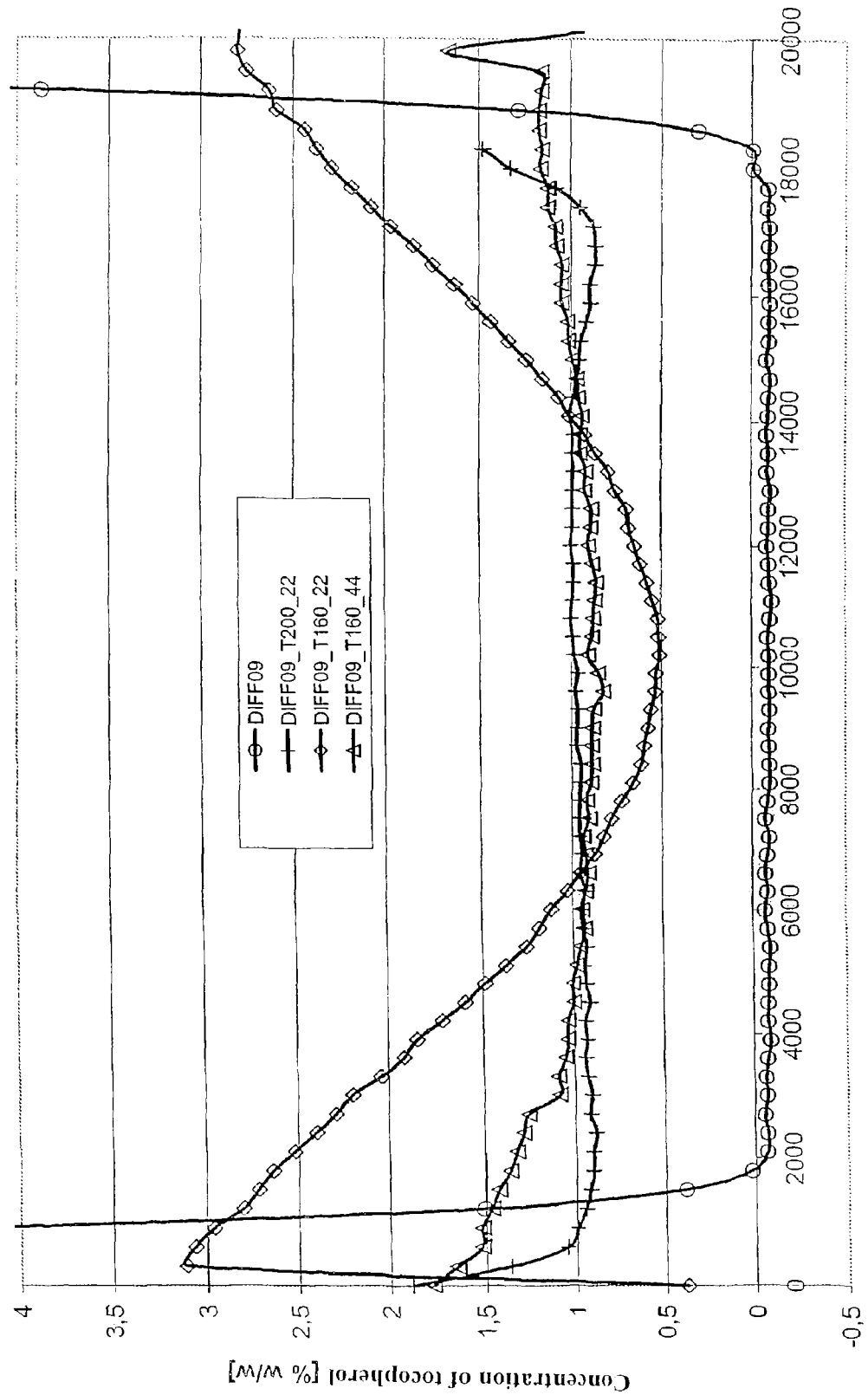
Figure 4:
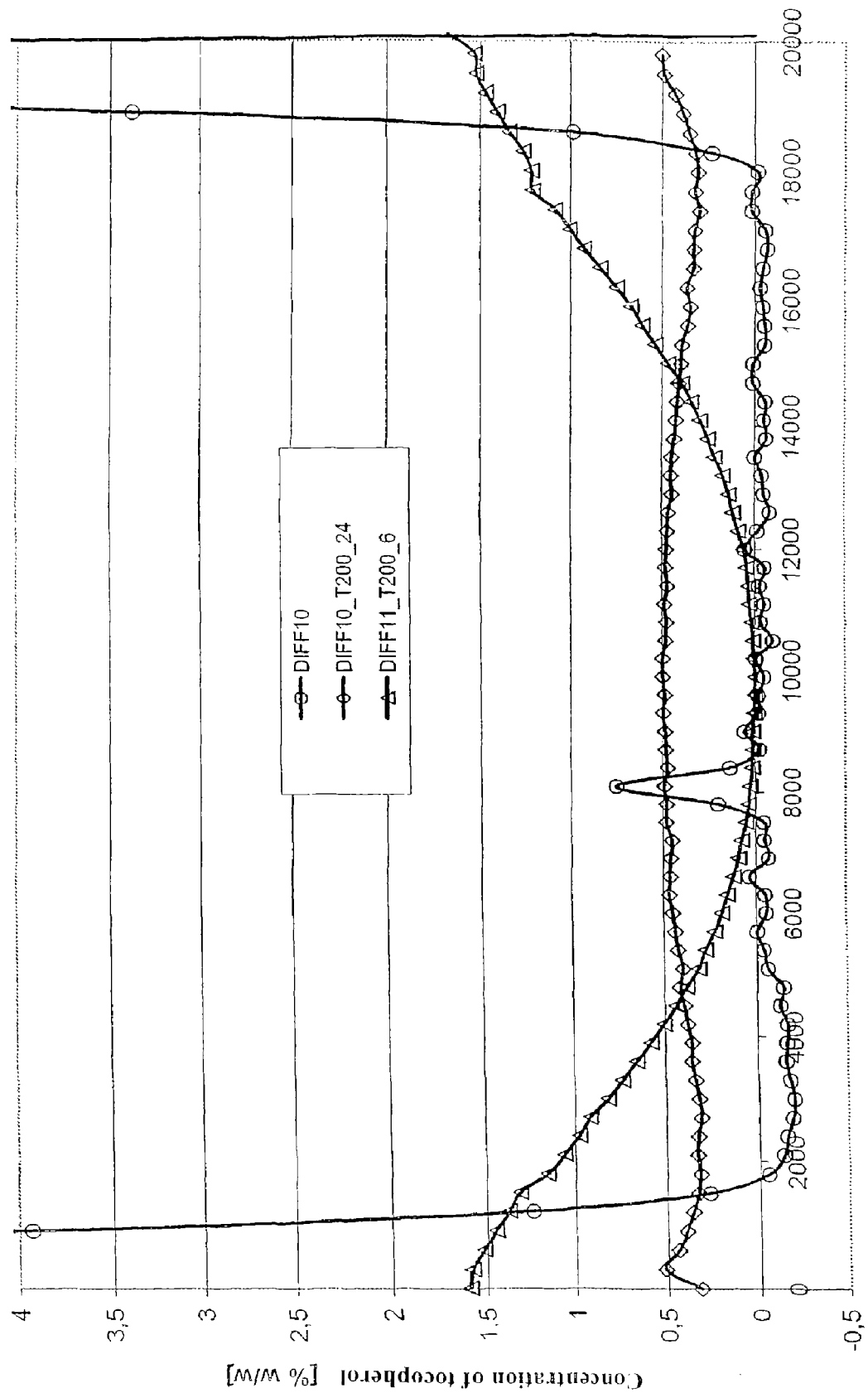

Therefore, an annealing process was carried out following the diffusion in order to achieve uniform distribution. For this purpose, the samples were first spiked with α-tocopherol in the autoclave, as described above, were then removed therefrom and were subsequently stored in a flask under a nitrogen atmosphere at different temperatures for different time intervals. In the autoclave, an edge layer exhibiting different thicknesses depending on the diffusion time and having a high concentration of α-tocopherol was thus generated via the temperature and was then distributed across the cube in the subsequent annealing process. Table 2 and FIGS. 2, 3 and 4 show the test parameters and the concentration profiles thus obtained, respectively, of the annealed samples.

TABLE 2

|  | Diffusion | | Annealing | |
| --- | --- | --- | --- | --- |
| Experiment | Temperature [° C.] | Duration of diffusion [h] | Temperature [° C.] | Annealing time [h] |
| DIFF09 | 130 | 2 | | |
| DIFF09_T160_22 | 130 | 2 | 160 | 22 |
| Dl1FF09_T160_44 | 130 | 2 | 160 | 44 |
| DIFF09_T200_22 | 130 | 2 | 200 | 22 |
| DIFF10 | 130 | 1 | | |
| DIFF10_T200_24 | 130 | 1 | 200 | 24 |
| DIFF11_T200_6 | 130 | 1.25 | 200 | 6 |

Figure 5:
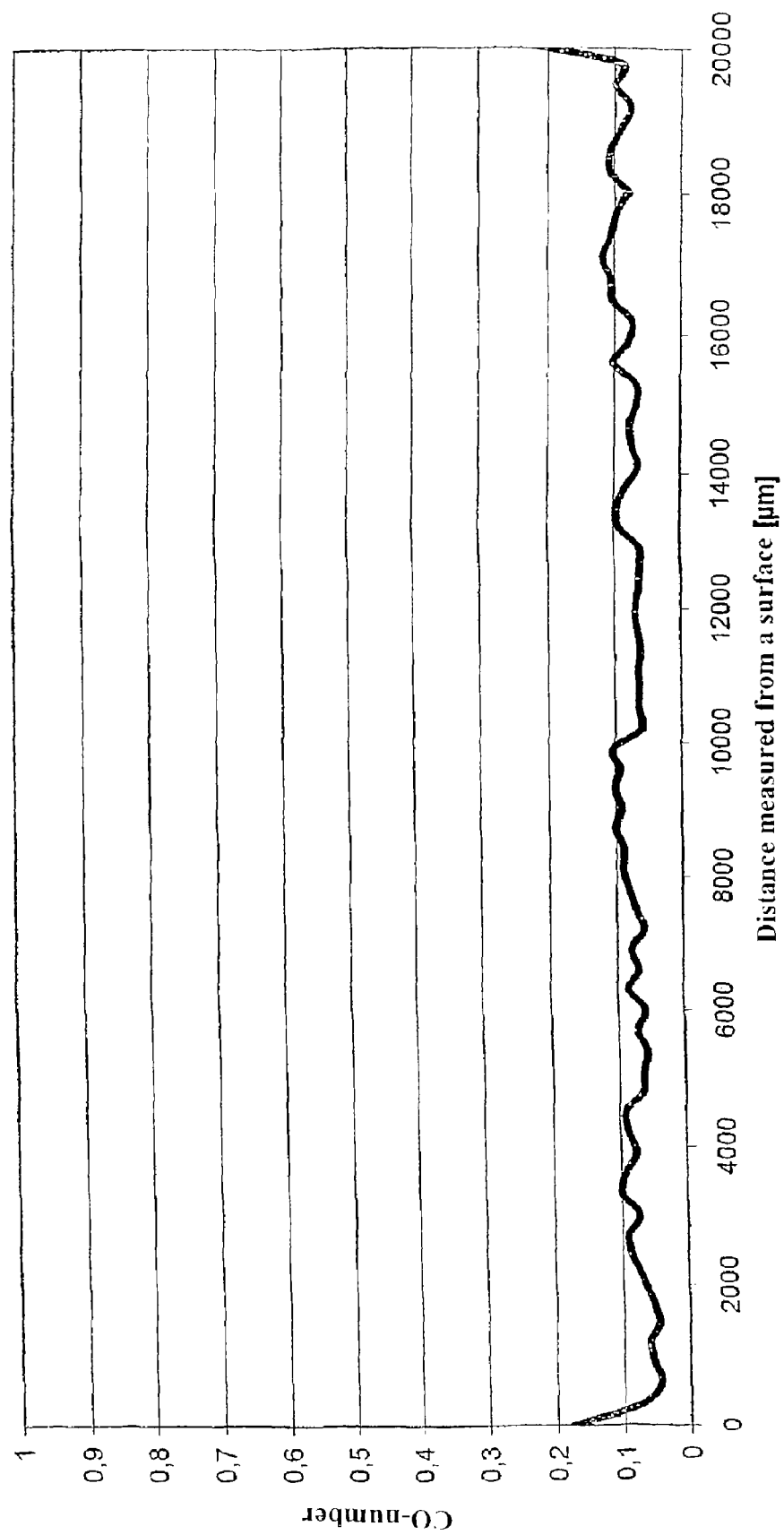
FIG. 5 shows the oxidation profile of a moulded body according to the invention.

Furthermore, the CO-numbers were determined in order to detect possible damage to the material sustained in the course of the annealing process. FIG. 5 shows the oxidation profile of the PE-cube of Experiment DIFF11_T200_6. When the inert atmosphere was carefully maintained, no oxidative damage to the material could be detected.

Based on the achieved results, it is apparent that, by varying the parameters diffusion time, temperature during diffusion, duration and temperature of the annealing process, the concentration profile of α-tocopherol in UHMW-PE may be adjusted at will within wide margins.

The concentration profile DIFF10_T200_24 in FIG. 4 shows, for example, a nearly homogeneous impregnation of the UHMW-PE cube with a stabilizer concentration of approx. 0.4% w/w, which can be considered as the optimum amount for many applications.

Production of a Homogeneously Impregnated Cube with a Concentration of 0.4% w/w of α-Tocopherol The autoclave is filled in the cold state with α-tocopherol and the cube is inserted such that it is engulfed completely by α-tocopherol. Subsequently, the autoclave is closed and flushed with nitrogen for 15 minutes. Upon completion of the flushing stage, a pressure of 15 bar is applied and the autoclave is heated to 130° C. As soon as 130° C. are reached, the temperature is kept constant for 60 minutes and is then cooled down to room temperature.

The cube is removed from the autoclave and is placed into a glass vessel which is flushed with nitrogen for 15 minutes. The vessel is closed and stored at 200° C. for 24 hours. After the expiry of this time period, it is cooled down to room temperature and the cube is removed from the vessel.

Introduction of α-Tocopherol into Crosslinked UHMW-PE with the Help of Supercritical $CO_2$ For the experiments, a laboratory autoclave with a capacity of 300 ml was used, which, for reasons of heating, was located in a furnace. The temperature was measured by a sensor attached to the exterior wall of the autoclave. A $CO_2$—high-pressure pump as well as a mechanical outlet valve were connected to the autoclave.

The UHMW-PE cubes were placed into the autoclave on a grid frame together with the weighed-in amount of α-tocopherol. Subsequently, the autoclave was placed into the furnace and slowly heated to the desired temperature, whereby the $CO_2$ pressure was applied at the same time. After reaching the desired temperature, the time measurement was started. After the expiry of the desired test period, the expansion process was started.

Expansion has to be effected at such a speed and temperature that neither a "tearing" of the UHMW-PE moulded body nor changes in the crystal structure are caused.

In the expansion process, the following procedure was used: After the expiry of the predetermined test period, the autoclave was detached from the $CO_2$ pump. This served for preventing an afterflow of cold carbon dioxide. Since only one mechanical valve was provided, it was impossible to carry out the required slow pressure decrease in a continuous fashion, therefore, the pressure was gradually decreased in a discontinuous fashion. Within a timeframe of 24 hours, the pressure was decreased approximately every hour by 20 bar within 30 seconds (with a relatively long interruption at night). In doing so, the temperature was always kept at the test temperature, on the one hand, due to the diffusion rate which was increased in this way and, on the other hand, in order to avoid structural changes caused by a crystallization of the material at a high $CO_2$ concentration. Only after the expansion process, the temperature was slowly (approx. within 3 hours) reduced to room temperature.

With the aid of controlled outlet valves, the expansion process can be optimized in temporal terms, whereby a certain minimum duration is necessary in any case.

Results:

Similarly as in experiments with conventional diffusion, the test temperature as well as the test duration significantly determine the diffusion rate and the penetration depth of α-tocopherol into crosslinked UHMW-PE. If the crystallite melting range is exceeded, the result is a significant increase in the velocity, as already described.

Figure 6:
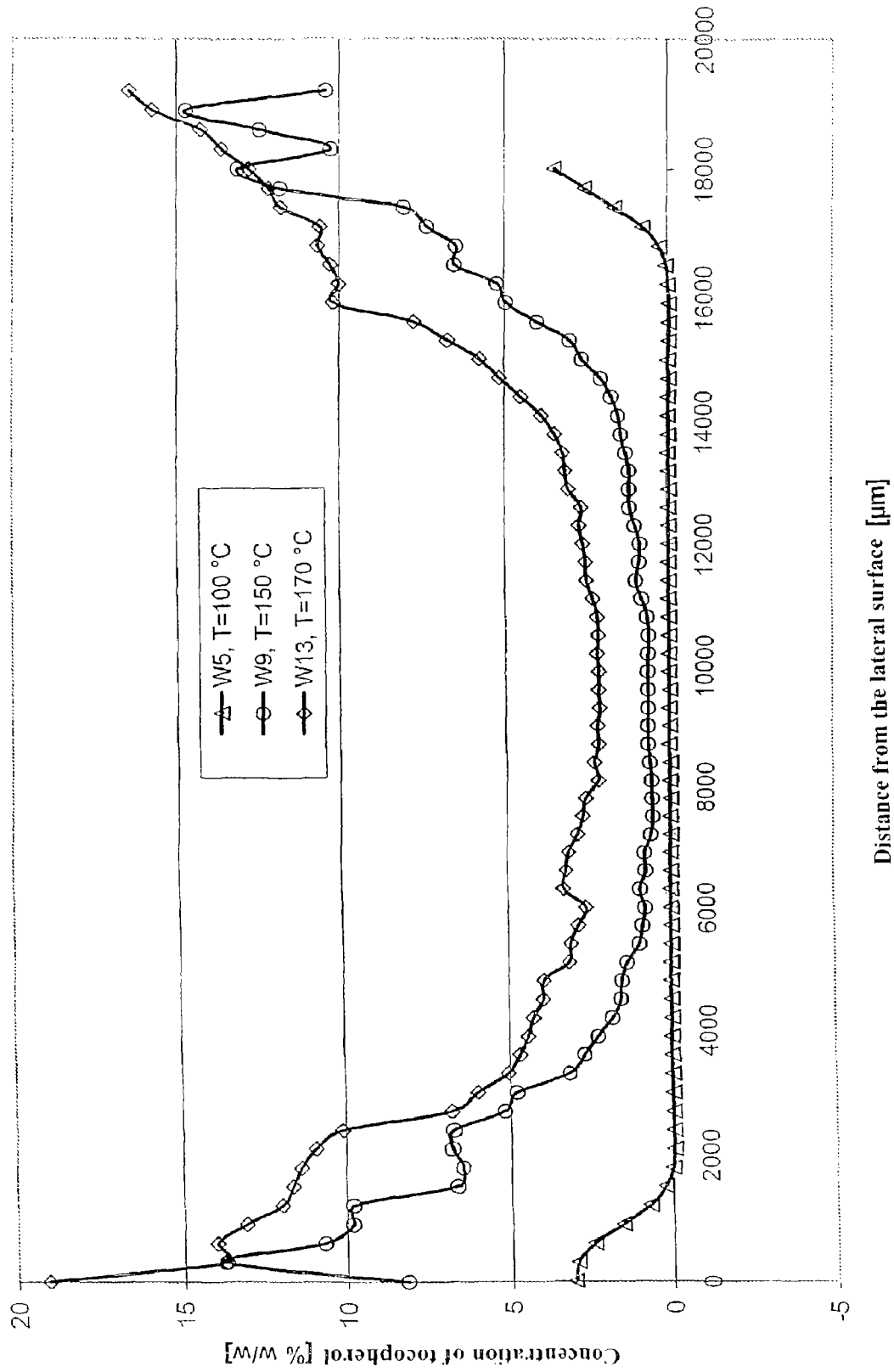

FIG. 6 shows the influence of the temperature on the introduction of α-tocopherol into the crosslinked UMW-PE. In Table 3, the respective test parameters are specified.

TABLE 3

| Experiment | Temperature [° C.] | Test duration [h] | Pressure [bar] |
| --- | --- | --- | --- |
| W5 | 100 | 4 | 300 |
| W9 | 150 | 4.25 | 300 |
| W13 | 170 | 4 | 300 |

Figure 7:
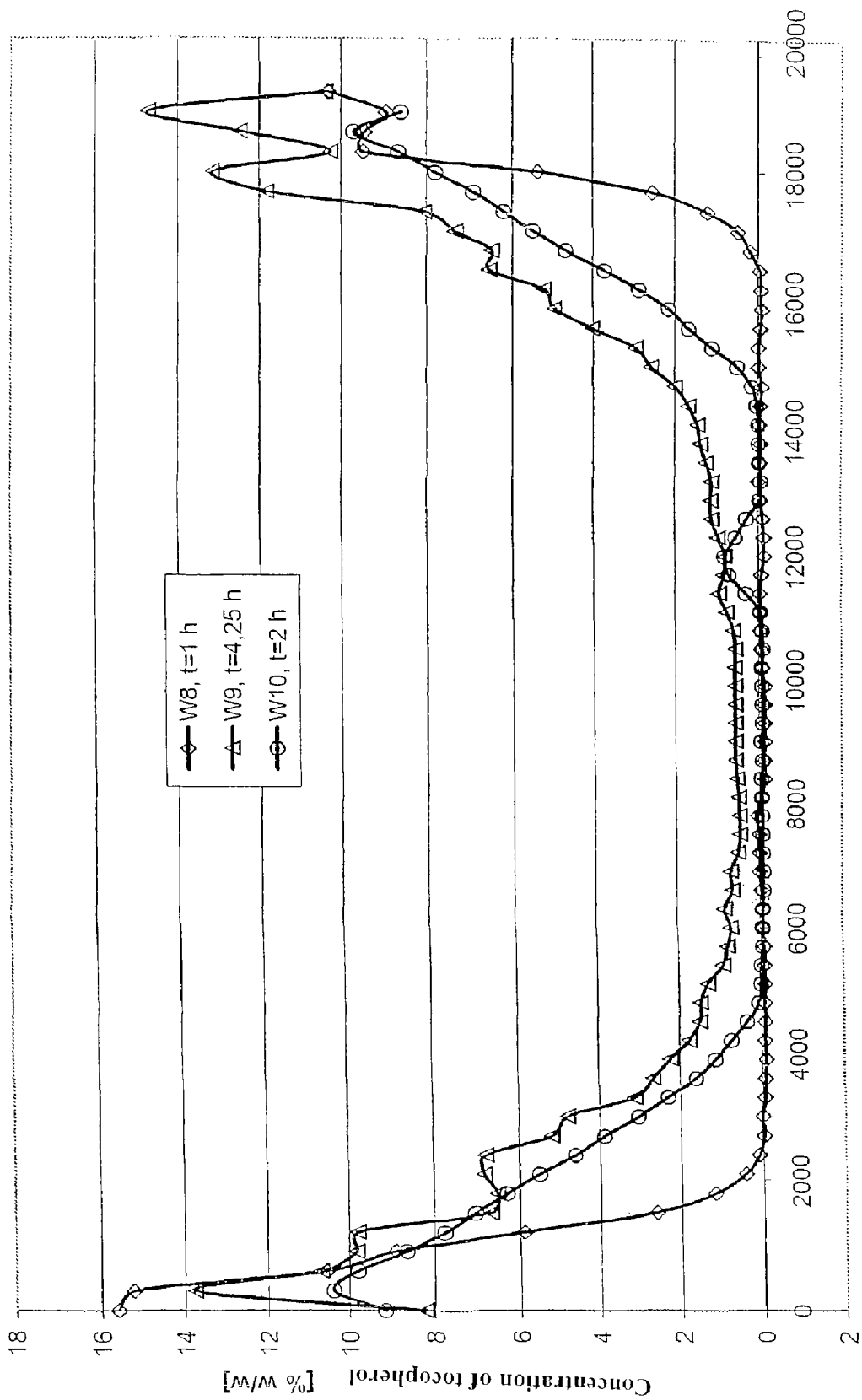

Varying the test duration primarily results in different penetration depths, as can be seen in FIG. 7 and Table 4.

TABLE 4

| Experiment | Temperature [° C.] | Test duration [h] | Pressure [bar] |
| --- | --- | --- | --- |
| W8 | 150 | 1 | 300 |
| W9 | 150 | 4.25 | 300 |
| W10 | 150 | 2 | 300 |

Figure 8:
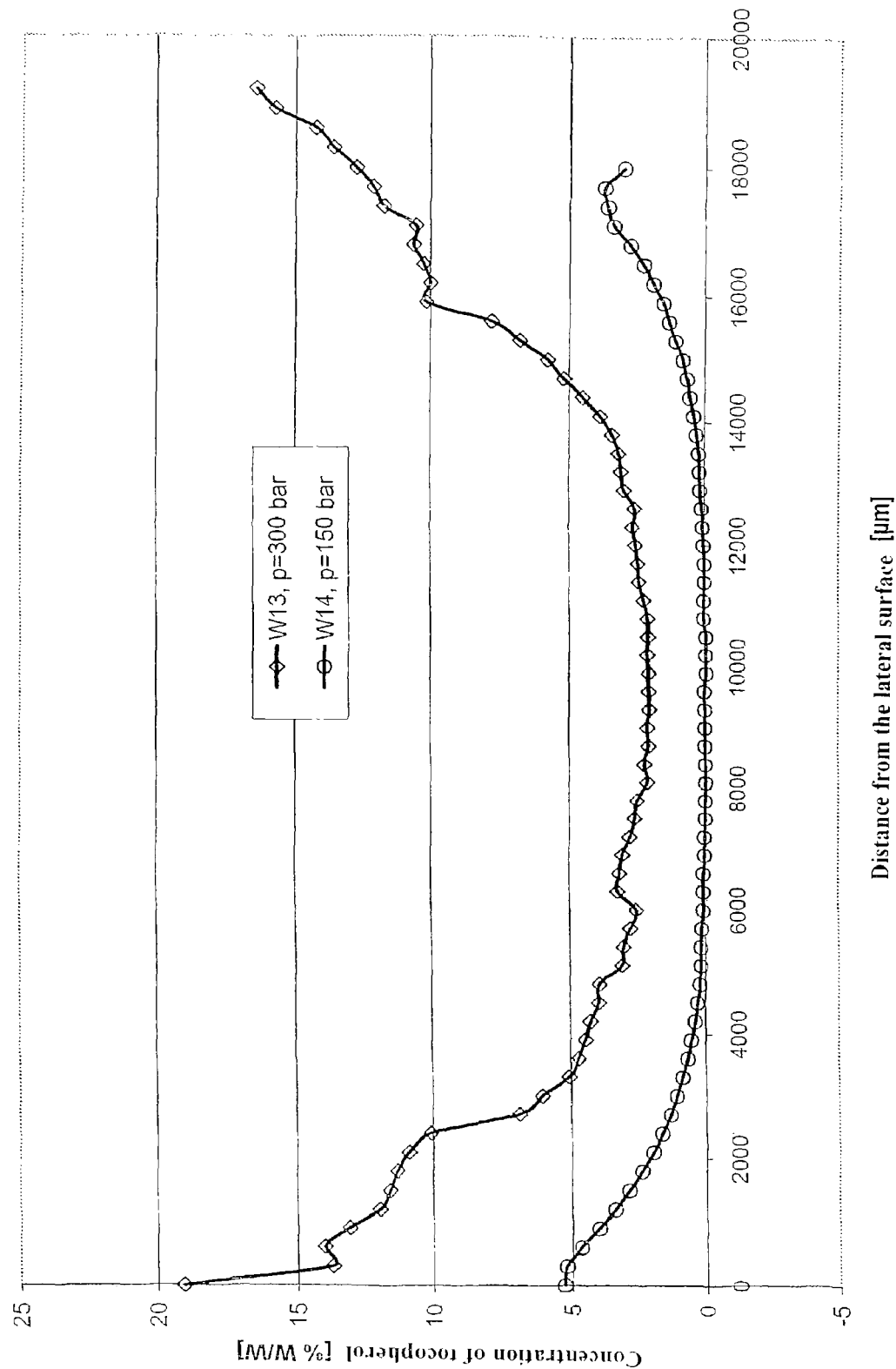

The influence of the pressure, which plays an important role during the introduction of α-tocopherol with $CO_2$, is varying. The pressure affects the density of $CO_2$ and hence—according to the above-indicated formula—the solubility of α-tocopherol in $CO_2$ as well as the diffusion rate. As can be seen clearly in FIG. 8, a decrease in pressure significantly reduces the amount of vitamin E which has diffused in. Therefore, the pressure was kept at 300 bar for all further experiments. Table 5 shows the test parameters of FIG. 8.

TABLE 5

| Experiment | Temperature [° C.] | Test duration [h] | Pressure [bar] |
| --- | --- | --- | --- |
| W13 | 170 | 4 | 300 |
| W14 | 170 | 3 | 150 |

Figure 9:
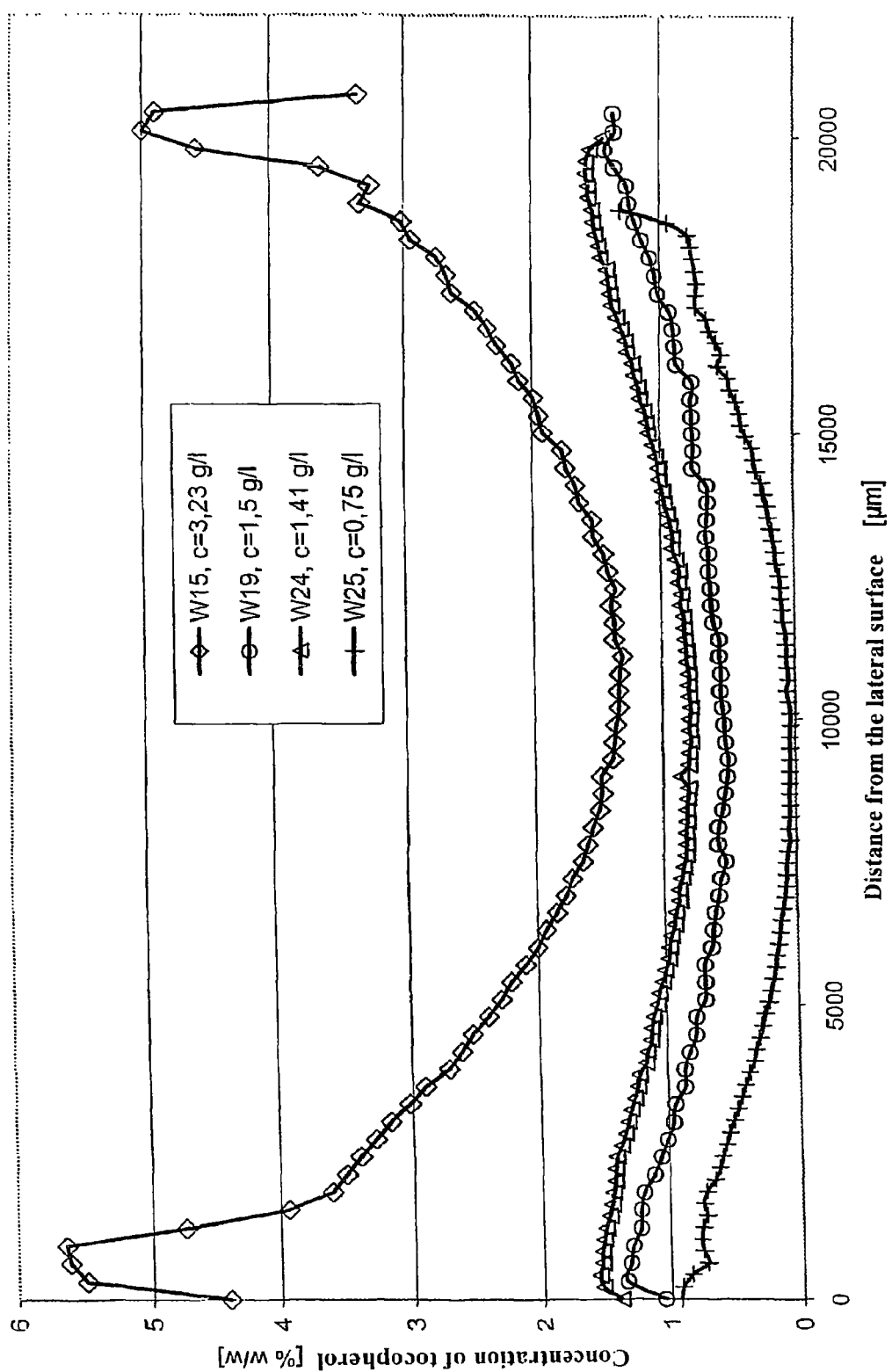

The most significant distinction from an introduction via conventional diffusion consists in that, due to the provision of α-tocopherol in the $CO_2$, the maximum concentration can be adjusted in the material; the $CO_2$ acts, so to speak, as a diluent. FIG. 9 (the respective test parameters are indicated in Table 6)

shows the results of experiments involving a different manner of providing α-tocopherol. A decrease in the concentration of α-tocopherol in the $CO_2$ leads to a decrease in the average concentration of α-tocopherol in the UHMW-PE.

TABLE 6

| Experiment | Temperature [° C.] | Test duration [h] | Pressure [bar] | α-tocopherol concentration [g/l] |
|---|---|---|---|---|
| W15 | 171 | 12 | 300 | 0.97 |
| W19 | 168 | 13.5 | 300 | 0.45 |
| W24 | 172 | 14 | 300 | 0.424 |
| W25 | 172 | 7 | 300 | 0.224 |

The achieved results show that α-tocopherol can be introduced as a stabilizer into crosslinked UHMW-PE by means of supercritical $CO_2$. By varying the four main influencing factors test duration, pressure, temperature and α-tocopherol concentration in the $CO_2$, the concentration profile of α-tocopherol in UHMW-PE may be adjusted at will within wide margins.

Since the maximum of the concentration distribution is adjusted primarily via the provision of α-tocopherol in the $CO_2$ rather than via the temperature, high temperatures and $CO_2$ pressures can be used in view of short process times. In order to homogeneously impregnate a UHMW-PE cube with an edge length of 2 cm, 12 hours are still necessary at 170° C. and a $CO_2$ pressure of 300 bar.

Special attention must also be paid to the expansion process, since a too rapid expansion can lead to the destruction of the material.

Production of a Homogeneously Impregnated Cube with a Concentration of 0.4% w/w of α-Tocopherol The cube is placed into the cold autoclave together with the α-tocopherol. The amount of vitamin E is weighed in such that the concentration in the $CO_2$ is equal to 0.75 g/l. Thereupon, the temperature and the pressure are raised slowly (approx. within one hour) to 170° C. and 300 bar, respectively. After 12 hours at 170° C. and 300 bar, the expansion process is started. For this purpose, the pressure is released within 24 hours at a constant temperature of 170° C. Subsequently, the temperature is decreased to room temperature within 3 hours.

The invention claimed is:

1. A process for the stabilization of crosslinked ultra-high molecular weight polyethylene with α-tocopherol, which comprises introducing α-tocopherol through diffusion into polyethylene which has been irradiated to obtain crosslinking, and annealing the polyethylene under an inert gas atmosphere following diffusion of α-tocopherol, wherein annealing is carried out at a temperature ranging from 160 to 200° C.

2. The process according to claim 1, wherein said diffusion is carried out under an inert gas atmosphere.

3. The process according to claim 1 or 2, wherein said diffusion of α-tocopherol is carried out at a temperature ranging from 100 to 200° C.

4. The process according to claim 1, wherein said α-tocopherol is allowed to diffuse into the polyethylene at 130° C. for 60 minutes, which polyethylene is subsequently annealed at 200° C. for 24 hours.

5. The process according to claim 1, wherein said α-tocopherol is allowed to diffuse into the polyethylene in the presence of supercritical $CO_2$.

6. The process according to claim 5, wherein said diffusion of α-tocopherol into the polyethylene is carried out at a temperature ranging from 100 to 180° C.

7. The process according to claim 5 or 6, wherein said diffusion of α-tocopherol into the polyethylene is carried out at a pressure ranging from 150 to 300 bar.

8. The process according to claim 5, wherein the temperature of the diffusion step is maintained while the $CO_2$ is being expanded.

* * * * *